(12) United States Patent
Rosenberg et al.

(10) Patent No.: US 8,843,197 B2
(45) Date of Patent: Sep. 23, 2014

(54) METHOD AND SYSTEM TO CORRECT CONTRACTILITY BASED ON NON-HEART FAILURE FACTORS

(75) Inventors: Stuart Rosenberg, Castaic, CA (US); Cecilia Qin Xi, San Jose, CA (US); Jong Gill, Valencia, CA (US); Brian Jeffrey Wenzel, San Jose, CA (US); Yelena Nabutovsky, Sunnyvale, CA (US); William Hsu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 756 days.

(21) Appl. No.: 13/049,774

(22) Filed: Mar. 16, 2011

(65) Prior Publication Data

US 2012/0239104 A1    Sep. 20, 2012

(51) Int. Cl.
  *A61N 1/365*    (2006.01)
  *A61B 5/02*     (2006.01)
  *A61B 5/042*    (2006.01)
  *A61N 1/362*    (2006.01)

(52) U.S. Cl.
  CPC ......... *A61N 1/36585* (2013.01); *A61N 1/36507* (2013.01); *A61B 5/042* (2013.01); *A61B 5/02028* (2013.01); *A61N 1/35678* (2013.01); *A61N 1/36564* (2013.01); *A61N 1/36521* (2013.01); *A61N 1/3627* (2013.01)
  USPC ........................................................ 607/18

(58) Field of Classification Search
  CPC ........... A61N 1/36585; A61N 1/36514; A61N 1/36564; A61N 1/36578; A61B 5/02028; A61B 5/02; A61B 5/02156; A61B 5/02158; A61B 5/0538; A61B 5/053
  USPC ............................................. 607/17–18, 23–24
  See application file for complete search history.

(56) References Cited

U.S. PATENT DOCUMENTS

| | | | | |
|---|---|---|---|---|
| 4,485,813 | A * | 12/1984 | Anderson et al. | 600/488 |
| 6,044,299 | A * | 3/2000 | Nilsson | 607/19 |
| 6,208,900 | B1 * | 3/2001 | Ecker et al. | 607/17 |
| 6,788,970 | B1 * | 9/2004 | Park et al. | 607/17 |
| 2005/0049646 | A1 * | 3/2005 | Czygan et al. | 607/27 |
| 2010/0004712 | A1 | 1/2010 | Zhao et al. | |
| 2011/0125208 | A1 * | 5/2011 | Karst et al. | 607/17 |

FOREIGN PATENT DOCUMENTS

EP    2143467 A1    1/2010

* cited by examiner

*Primary Examiner* — Carl H Layno
*Assistant Examiner* — Jessica Anthony

(57) ABSTRACT

A method for trending heart failure measures cardiogenic impedance (CI) and obtains signals representing estimates for or direct measurements of at least one of cardiac volume and pressure of the heart when the CI measurements were obtained. The method identifies correction factors based on the signals and applies the correction factors to the contractility estimates. A system for trending heart failure includes a contractility module to determine contractility estimates from CI measurements taken along at least a first vector through a heart, and a collection module to receive signals representing estimates for or direct measurements of at least one of cardiac volume and pressure of the heart when the CI measurements were obtained. The system further includes a factor module to identify correction factors based on the signals and a correction module to apply the correction factors to the contractility estimates.

19 Claims, 7 Drawing Sheets

METHOD AND SYSTEM TO CORRECT CONTRACTILITY BASED ON NON-HEART FAILURE FACTORS

FIELD OF THE INVENTION

Embodiments of the present invention generally relate to methods and systems to correct contractility measurements.

BACKGROUND OF THE INVENTION

It has been proposed, and is being tested and implemented in heart failure diagnostics to use features of the cardiogenic impedance (CI) signal for estimating contractility. Specifically, it has been proposed to use trended changes in CI-derived contractility to contribute to diagnosis and prediction of worsening heart failure events. Moreover, it may be desirable to determine pacing sites or timing intervals based on CI-derived contractility, to diagnose ischemic and/or arrhythmic events based on acute or sub acute (i.e. seconds-to-minutes time frame) changes in CI, or to guide or activity responsive changes to programmed parameters based on CI-derived contractility, among other applications.

Heretofore, it has been difficult to estimate quantities related to contractility. For instance, contractility may be used to determine information related to the strength or speed of contraction of an isolated myocyte, or alternately to local, regional, or global myocardial pumping function. Further, the term contractility has been used in scientific literature to refer to pulse pressure, rate of pressure rise, peak generated pressure, stroke volume, systolic or pre-ejection time intervals, and even synchrony, all as indicators of "contractility."

However, a number of non-heart failure (non-HF) factors contribute to the various measurable values from which contractility is derived. These non-HF factors include preload, afterload, metabolic state, heart rate, neurohormonal influences, and the like. While these non-HF factors do exert real influence on cardiac performance, it is important to separate the effects of non-HF factors from fundamental changes to the myocardium that are to be measured. For example, it is desirable to use contractility to identify myocardium changes due to worsening heart failure, due to optimized (or non-optimized) pacing, and the like. Therefore, methods and systems are needed that provide a true and independent assessment of contractility, unaffected by non-HF factors.

This invention describes a set of methods using various sensors/measurements available on the implanted device in conjunction with CI to remove confounding factors from contractility estimates, with specific examples given as to how the methods can be applied to a heart failure trending diagnostic.

SUMMARY

In accordance with one embodiment, CI measurements are obtained for predetermined vectors and at predetermined intervals. Features from the CI measurements are extracted that relate to contractility. In addition, other data (surrogate signals) are collected near the time of the CI measurements. Such data includes Z0 or average impedance values, heart rate, respiration rate, activity level, posture, paced versus sensed rhythm status, and additional CI vectors. These additional data are used to derive estimates or surrogates for cardiac volumes and pressures, especially at end diastole (preload); systemic pressure (afterload); and oxygen requirements or work load (demand). Methods and systems are described that remove or normalize for the effects of each non-HF factor on estimated contractility, thereby improving the estimate of the "raw" cardiac performance trend independent of other non-HF factors. It is postulated that trending such raw cardiac performance will be both more sensitive and more specific to detecting worsening heart failure.

In accordance with one embodiment, a method is provided for trending heart failure based on heart contractility information. The method measures cardiogenic impedance (CI) measurements along at least a first vector through a heart over a period of time. The method determines contractility estimates from the CI measurements where the contractility estimates relates to contractility of the heart. The method further obtains surrogate signals representing estimates for at least one of cardiac volume and pressure of the heart when the CI measurements were obtained. The method identifies correction factors based on the surrogate signals and applies the correction factors to the contractility estimates to produce contractility trend values over the period of time.

In accordance with one embodiment, the method further illustrates a series of contractility trend values as a heart failure trend over the period of time. The method's applying operation adjusts the contractility estimates, based on the correction factors, to remove non-HF effects due to at least one of preload effects, after-load effects and supply-demand effects. The method provides surrogate signals that represent estimates of end diastolic volume, wherein the CI measurements and associated surrogate signals are obtained concurrently. The applying operation removes preload effects from the contractility estimates wherein the preload effects relate to at least one of the end diastolic volume and pressure which results in stretching of cardiomyocytes prior to depolarization and contraction. The method comprises surrogate signals that represent estimates of blood pressure, wherein the CI measurements and associated surrogate signals are obtained concurrently. The method provides the applying operation which removes after-load effects from the contractility estimates wherein the after-load effects relate to load against which the heart contracts. The method comprises surrogate signals which represent estimates of heart rate and stroke volume, wherein the CI measurements and associated surrogate signals are obtained concurrently. The method provides the applying operation which removes supply-demand effects from the contractility estimates.

The method further comprises surrogate signals that represent estimates of at least one of heart rate, stroke volume, patient activity and respiration and wherein the CI measurements and associated surrogate signals are obtained concurrently to ascertain differences between changes in demand versus supply of oxygen.

In accordance with one embodiment, the method provides the identifying operation which determines the identifying whether a patient is in a rest state or an active state. The method further provides the applying operation that applies a heart rate correction factor when the patient is in the rest state and the applying operation applies a cardiac output correction factor when the patient is in the active state.

The method comprises the surrogate signals representing at least one of a low frequency component of intracardiac impedance measured along at least one surrogate vector through the heart, an average intracardiac impedance measured along at least one surrogate vector through the heart, heart rate, respiration rate, an activity level of the patient, a posture of the patient, a paced versus sensed rhythm status, and a secondary CI measurement measured along at least one surrogate vector through the heart.

In accordance with one embodiment, a system for trending heart failure based on heart contractility information is provided which comprises inputs to receive cardiogenic impedance (CI) measurements taken along at least a first vector through a heart over a period of time. The system includes a contractility module to determine contractility estimates from the CI measurements where the contractility estimates relating to contractility of the heart. The system includes a surrogate module to receive surrogate signals representing estimates for at least one of cardiac volume and pressure of the heart when the CI measurements were obtained. The system includes a factor module to identify correction factors based on the surrogate signals and a correction module to apply the correction factors to the contractility estimates to produce contractility trend values over the period of time.

The system further comprises a display to illustrate a series of contractility trend values as a heart failure trend over the period of time. The system includes the correction module that adjusts the contractility estimates, based on the correction factors, to remove non-HF effects due to at least one of preload effects, after-load effects and supply-demand effects.

The system provides the surrogate signals which represent estimates of end diastolic volume, wherein the CI measurements and associated surrogate signals are obtained concurrently and the correction module removes preload effects from the contractility estimates. The preload effects relate to at least one of the end diastolic volume and pressure which results in stretching of cardiomyocytes prior to depolarization and contraction.

The surrogate signals represent estimates of blood pressure, wherein the CI measurements and associated surrogate signals are obtained concurrently, and the correction module removes after-load effects from the contractility estimates, the after-load effects relating to load against which the heart contracts. The system further provides that the surrogate signals represent estimates of heart rate and stroke volume, wherein the CI measurements and associated surrogate signals are obtained concurrently and the correction module removes supply-demand effects from the contractility estimates.

The system further includes the surrogate signals which represent estimates of at least one of heart rate, stroke volume, patient activity and respiration and wherein the CI measurements and associated surrogate signals are obtained concurrently to ascertain differences between changes in demand versus supply of oxygen.

The system provides the factor module that identifies whether a patient is in a rest state or an active state wherein the correction module applies a heart rate correction factor when the patient is in the rest state and wherein the correction module applies a cardiac output correction factor when the patient is in the active state. The system further includes the surrogate signals which represent at least one of a low frequency component of intracardiac impedance measured along at least one surrogate vector through the heart, an average intracardiac impedance measured along at least one surrogate vector through the heart, heart rate, respiration rate, an activity level of the patient, a posture of the patient, a paced versus sensed rhythm status, and a secondary CI measurement measured along at least one surrogate vector through the heart. The system further includes the surrogate signals that are obtained by identifying features from the CI measurements.

DETAILED DESCRIPTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. The following detailed description is, therefore, not to be taken in a limiting sense, and the scope of the present invention is defined by the appended claims and their equivalents.

Throughout, the terms "a" or "an" shall be used, as is common in patent documents, to include one or more than one. Throughout, the term "or" shall be used to refer to a nonexclusive or, unless otherwise indicated. Throughout, the term "measured impedance" shall refer to intracardiac and/or intrathoracic impedance measurements directly measured from a combination of electrodes positioned within the heart, proximate to the heart and/or within the chest wall. Throughout, the term "derived impedance" shall refer to intracardiac and/or intrathoracic impedance that is not directly measured, but instead is mathematically derived based on measured impedances as described throughout the present specification.

Figure 1:
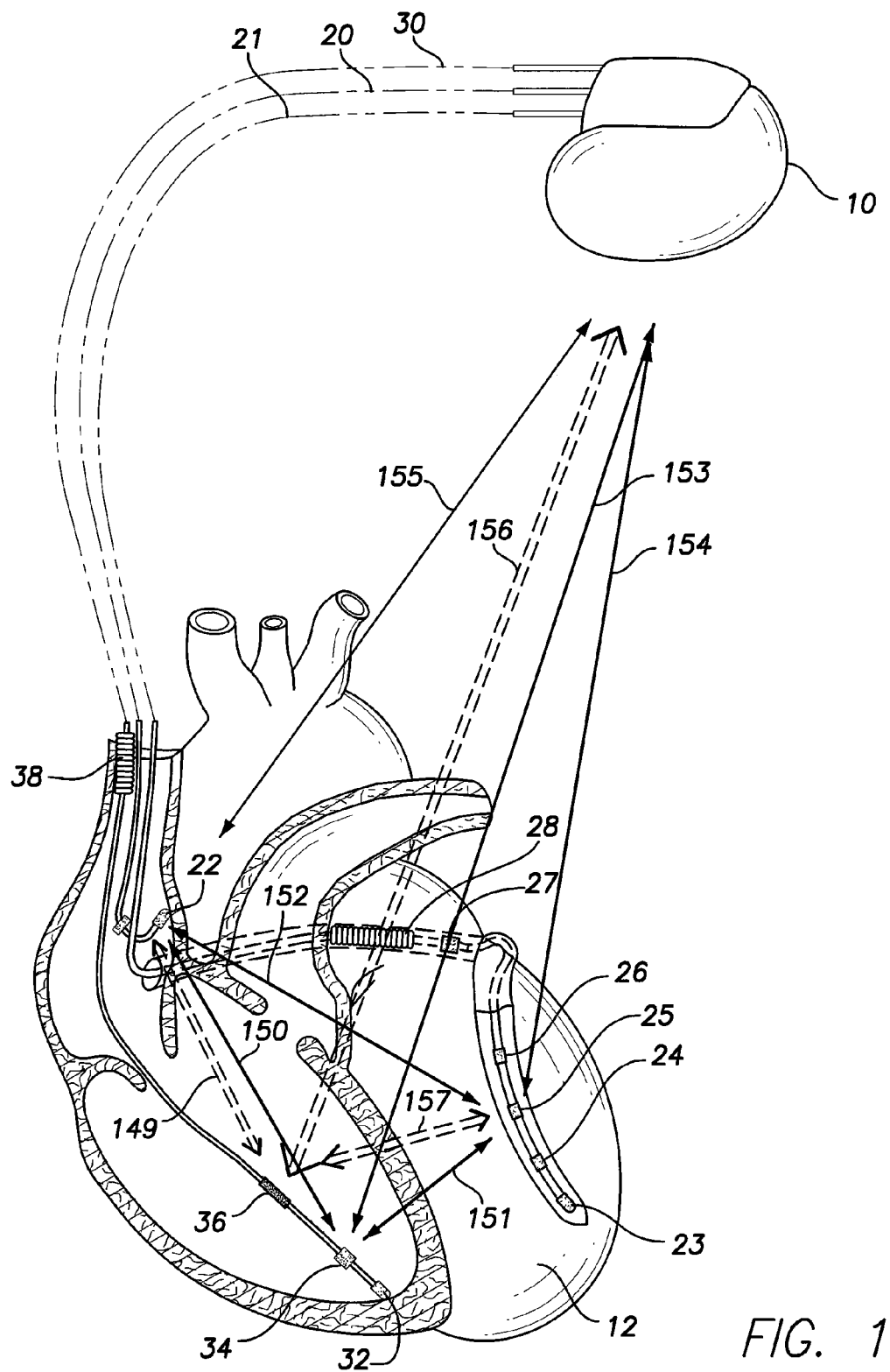
FIG. 1 illustrates a simplified diagram of an implantable medical device in electrical communication with leads implanted in or proximate a patient's heart.

FIG. 1 illustrates a simplified diagram of an IMD 10 in electrical communication with three leads 20, 21 and 30 implanted in or proximate to a patient's heart 12 for delivering multi-chamber stimulation (e.g. pacing, ATP therapy, high voltage shocks and the like) according to an embodiment. The stimulation may include pacing pulses that are delivered along one or more pacing vectors. Optionally, the stimulation may include ATP pulses or a high voltage shock that is delivered along one or more ATP therapy vectors, cardioverter vectors or defibrillation vectors. The IMD 10 may be a pacing device, a pacing apparatus, a cardiac rhythm management device, an implantable cardiac stimulation device, an implantable cardioverter/defibrillator (ICD), a cardiac resynchronization therapy (CRT) device, a monitoring device and the like. The IMD 10 is programmable, by an operator, to set certain operating parameters, as well as therapy-related parameters. The IMD 10 is configured to operate with various configurations of leads. Exemplary lead configurations are shown in the Figures. The IMD 10 is configured to sense various types of information and deliver various types of therapies. For example, the IMD 10 may sense intracardiac electrogram signals, impedances and the like.

In FIG. 1, the IMD 10 is coupled to an RA lead 20 having at least an atrial tip electrode 22, which typically is implanted in the patient's right atrial appendage. The IMD 10 is coupled to an LV lead 21 that includes various electrodes, such as an LV tip electrode 23, intermediate LV electrodes 24-26, and LA electrodes 27-28. The LV lead 21 may sense atrial and ventricular cardiac signals and cardiogenic impedances and deliver left ventricular therapy using the LV tip electrode 23, the intermediate LV electrodes 24-26, and the LA electrodes 27 and 28. The LV and LA electrodes 23-28 may be used as sensing sites, where cardiac signals and/or cardiogenic impedances are sensed, and/or may be used as pacing and/or shock therapy sites. A right ventricular lead 30 may include one or more of an RV tip electrode 32, an RV ring electrode 34, and a superior vena cava (SVC) coil electrode 38 (also known as a RA coil electrode). The right ventricular lead 30 is capable of sensing cardiac signals and/or cardiogenic impedances, and delivering stimulation in the form of pacing and shock therapy to the SVC and/or right ventricle.

Optionally, more or fewer electrodes may be utilized. The LV electrodes may be separated further apart or positioned closer to one another. Optionally, all or a portion of the LV electrodes may be shifted along the LV lead 21 until positioned proximate to the mitral valve, aortic valve, or the left atrial ports to/from the pulmonary veins. The LV lead 21 may be inserted directed into the LV chamber or inserted into a vein or artery extending along the heart wall proximate to the left ventricle. Optionally, the LV lead 21 may be coupled to a patch or mesh net electrode that is secured to or located adjacent to an exterior wall of the left ventricle and/or the left atrium.

Embodiments are described herein, whereby multiple electrodes are utilized to sense impedance along multiple sensing vectors. CI measurements, that are collected along the sensing vectors, are utilized to derive contractility estimates.

The IMD 10 defines sensing vectors between various combinations of two or more electrodes 22-28, 32, 34 and 38, and the housing of the IMD 10. FIG. 1 illustrates examples of sensing vectors 149-157. The sensing vectors 149-157 represent paths (generally a linear path) between at least two points. The IMD 10 obtains one or more impedance measurements along the sensing vectors 149-159 which extend through a substantial majority of the aortic vessels and the heart 12. An individual measured impedance represents the impedance of the walls of the heart 12, the blood in the heart 12 and any external tissue or muscle through which the corresponding sensing vector extends.

The sensing vector 150 extends between the RA electrode 22 and the RV electrode 34. The sensing vector 151 extends between the RV electrode 34 and the LV electrode 25. The sensing vector 152 extends between the LV electrode 25 and the RA electrode 22. The sensing vector 153 extends between the RV electrode 34 and the CAN electrode of the IMD 10. The sensing vector 154 extends between the LV electrode 25 and the CAN electrode. The sensing vector 155 extends between the RA electrode 22 and the CAN. Optionally, alternative and/or additional electrodes may be used to form alternative and/or additional sensing vectors.

The sensing vector 156 extends between the CAN electrode of the IMD 10 and an electrode site 36. The sensing vector 149 extends between the RA electrode 122 and a virtual electrode site 36. The sensing vector 157 extends between the LV electrode 25 and the virtual electrode site 36.

Each LV and RV electrode 22-38 represents a potential sensing site and/or therapy site. When functioning as a sensing site, the corresponding LV and/or RV electrode sense signals that are utilized to obtain impedance measurements. The sensing sites differ based on the type of device and type of detection algorithm utilized.

The impedance measured along the sensing vectors 149-157 may be expressed in terms of ohms. Alternatively, the impedance may be expressed as an admittance measurement. The admittance may be inversely related to the impedance. The impedance measured may vary based on a variety of factors, including the amount of fluid in one or more chambers of the heart 12 and/or thoracic space. As a result, the impedance measurement may be indicative of LAP. As more blood fills the left atrium and pulmonary veins, the LAP increases. Blood is more electrically conductive than the myocardium of the heart 12. Consequently, as the amount of blood in the left atrium increases, the LAP increases and the impedance measured along the sensing vector decreases. Conversely, decreasing LAP may result in the impedance measurement increasing as there is less blood in the left atrium and pulmonary veins. Optionally, impedance measurements along various sensing vectors may be utilized to monitor and characterize pressure and blood flow in other chambers of the heart, such as RA, RV, LA and/or LV pressure, blood flow, and/or chamber dimension or volume.

Figure 2:
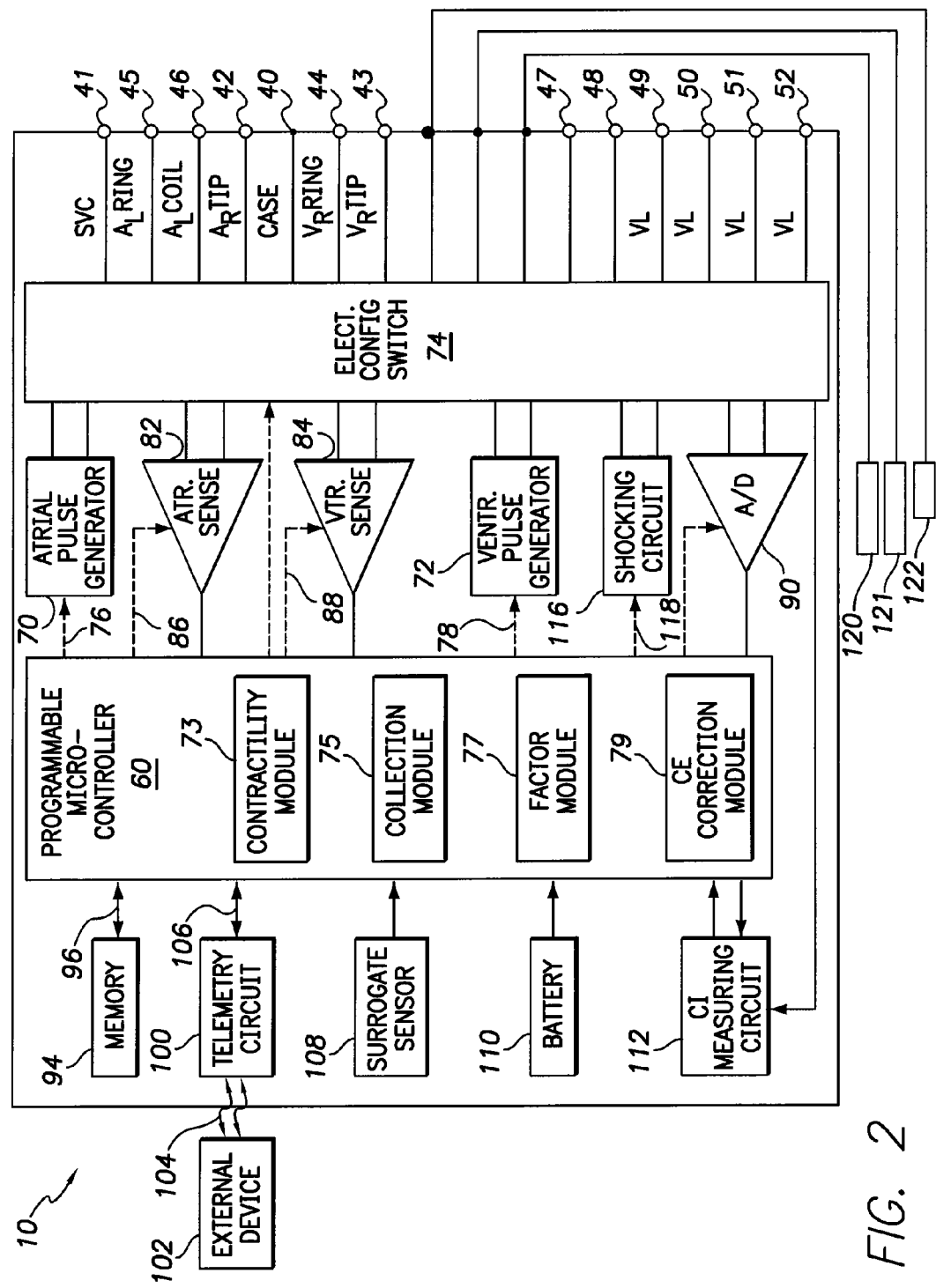
FIG. 2 illustrates a block diagram of the IMD of FIG. 1.

FIG. 2 illustrates a block diagram of the IMD 10, which is capable of treating one or both of fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

The housing 40 for the stimulation IMD 10 is often referred to as the "can", "case" or "case electrode" and may be programmably selected to act as the return electrode for some or all sensing modes. The housing 40 may further be used as a return electrode alone or in combination with one or more of the electrodes of FIG. 1 for shocking purposes. The housing 40 further includes a connector (not shown) having a plurality of terminals 41-52. To achieve sensing, pacing and shocking in desired chambers of the heart, the terminals 41-52 are selectively connected to corresponding combinations of electrodes 22-38.

The IMD 10 includes a programmable microcontroller 60 that controls the various modes of sensing and stimulation therapy. The microcontroller 60 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 60 includes the ability to process or monitor input signals (data) as controlled by a program code stored in memory. The details of the design and operation of the microcontroller 60 are not critical to the present invention. Rather, any suitable microcontroller 60 may be used. The microcontroller 60 analyzes sensed signals and determines when an arrhythmia (e.g., fibrillation) is occurring. The microcontroller 60 detects arrhythmias, such as ventricular tachycardia (VT), bradycardia and ventricular fibrillation (VF). The microcontroller 60 may perform morphology detection to analyze the morphology of the cardiac signal, including detecting R wave peaks and/or detecting T wave features of interest, such as onset, peak, etc.

An atrial pulse generator 70 and a ventricular pulse generator 72 generate pacing and ATP stimulation pulses for delivery by desired electrodes. The electrode configuration switch 74 (also referred to as switch bank 74) controls which terminals 41-52 receive impedance measurement, electrical signals, shocks or pacing pulses. The pulse generators 70 and 72 are controlled by the microcontroller 60 via appropriate control signals 76 and 78, respectively, to trigger or inhibit stimulation pulses. The microcontroller 60 controls the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 74 connects the sensing electronics to the desired terminals 41-52 of corresponding sensing electrodes 22-38. For example, terminals 49-52 may be coupled to LV electrodes 23-26. The switch 74 may connect terminals 41-52 to one or more ventricular sensing circuits 84, which provide cardiac signals, representative of cardiac activity, to the microcontroller 60. The circuit 84 may amplify, filter, digitize and/or otherwise process the sensed cardiac signals from the LV electrodes 23-26. The circuit 84 may provide separate, combined or difference signals to the microcontroller 60 representative of the sensed signals from the LV electrodes 23-26. The circuit 84 may also receive sensed signals from RV electrodes 32 and 34 through terminals 43 and 44. The atrial sensing circuit 82 is connected through the switch 74 terminals 42 and 45-46 to desired RA and/or LA electrodes 22 and 27-28 to sense RA and/or LA cardiac activity. The switch 74 also connects various combinations of the electrodes 22-38 to an impedance measurement circuit 112.

An impedance measuring circuit 112 collects CI measurements between corresponding multiple combinations of electrodes 22-38. For example, the impedance measuring circuit 112 may collect a measured impedance for each or a subset of the sensing vectors 149-157. The CI measurements are taken along one or more vectors through the heart over a period of time. The CI measurements are supplied to the controller 60.

Atrial sensing circuits 82 and ventricular sensing circuits 84 may also be selectively coupled to the right atrial lead 20, LV lead 21, and the RV lead 30, through the switch 74 for detecting the presence of cardiac activity in each of the four chambers of the heart. The switch 74 determines the "sensing polarity" of the cardiac signal by selectively closing the appropriate switches. The outputs of the atrial and ventricular sensing circuits 82 and 84 are connected to the microcontroller 60 which, in turn, is able to trigger or inhibit the atrial and ventricular pulse generators 70 and 72, respectively. The sensing circuits 82 and 84, in turn, receive control signals over signal lines 86 and 88 from the microcontroller 60 for purposes of controlling the gain, threshold, the polarization charge removal circuitry (not shown), and the timing of any blocking circuitry (not shown) coupled to the inputs of the sensing circuits, 82 and 86.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external IMD 102. The data acquisition system 90 samples cardiac signals across any pair of desired electrodes. The microcontroller 60 further controls a shocking circuit 116 by way of a control signal 118. The shocking circuit 116 generates stimulating pulses of low (up to 0.5 Joules), moderate (0.5-10 Joules), or high energy (11 to 40 Joules), as controlled by the microcontroller 60. Stimulating pulses are applied to the patient's heart 12 through at least two shocking electrodes, and as shown in this embodiment, selected from the left atrial (LA) coil electrode 28, the RV coil electrode 36, the SVC coil electrode 38 and/or the housing 40.

The microcontroller 60 is further coupled to a memory 94 by a suitable data/address bus 96. The memory 94 stores programmable operating, impedance measurements, impedance derivation and therapy-related parameters used by the microcontroller 60. The operating and therapy-related parameters define, for example, surrogate signals, contractility estimates, models, length force curves, correction factors, trend values, pacing pulse amplitude, pulse duration, electrode polarity, rate, sensitivity, automatic features, arrhythmia detection criteria, and the amplitude, wave shape and vector of each stimulating pulse to be delivered to the patient's heart 12 within each respective tier of therapy.

The operating and therapy-related parameters may be non-invasively programmed into the memory 94 through a telemetry circuit 100 in telemetric communication with the external device 102, such as a programmer, trans-telephonic transceiver, or a diagnostic system analyzer. The telemetry circuit 100 is activated by the microcontroller 60 by a control signal 106. The telemetry circuit 100 advantageously allows intracardiac electrograms, CI measurements, surrogate signals, contractility estimates, correction factors, models, trend values and status information relating to the operation of the IMD 10 (as contained in the microcontroller 60 or memory 94) to be sent to and from the external device 102 through an established communication link 104.

The IMD 10 includes one or more surrogate sensors 108. The surrogate sensor(s) 108 produces surrogate signals representative of estimates for at least one of cardiac volume and pressure of the heart when the CI measurements were taken. For example, the surrogate sensor 108 may sense estimates of end diastolic volume, blood pressure, heart rate, stroke volume, patient activity, respiration rate and the like. Optionally, the surrogate sensor 108 may produce surrogate signals by identifying features of interest from the CI measurements. For example, the sensor 108 may collect and filter impedance signals along one or more impedance sensing vectors (e.g., as shown in FIG. D). The sensor 108 may include a low-pass, band pass and/or high pass filter to filter the CI measurements and produce non-contractility information.

The sensors 108 may include one or more of an accelerometer, a pressure sensor, a heart sound sensor, a pulse oximetry sensor, a flow sensor and the like. While a sensor 108 is shown within the housing of the IMD 10, optionally, one or more sensors 108 may be located outside the IMD and coupled to the IMD 10 through a connector. The sensor 108 may detect a level of or changes in cardiac output, a level of changes in the physiological condition of the heart, or a level of or changes in activity (e.g., detecting sleep and wake states). The battery 110 provides operating power to all of the circuits shown in FIG. 2.

The controller 60 includes, among other things, a contractility module 73, a collection module 75, a factor module 77 and a contractility estimate (CE) correction module 79. The contractility module 73 receives a set or group of CI measurements for a CE period of time (e.g., one cardiac cycle, one minute, multiple cardiac cycles, etc.) which define an impedance waveform. The contractility module 73 analyzes the impedance waveform to derive a contractility estimate from the CI measurements for the CE period of time. The contractility module 73 may continuously or periodically receive new sets or groups of CI measurements and derive contractility estimates for each set or group of CI measurements. The operations performed by the contractility module 73 are discussed below in more detail in connection with FIG. A. In accordance with embodiments described herein, the CI measurements are collected over a predetermined period of time. The CI measurements may then be plotted as an impedance waveform over the predetermined period of time. Estimates of contractility are determined from the CI measurements based on one or more features from the impedance waveform.

The collection module 75 receives physiologic and/or surrogate signals from one or more sensors. Optionally, the physiologic and/or surrogate signals may be received, through the switch 74, from one, multiple or combinations of the electrodes 22-36 illustrated in FIG. 1. Alternatively, the physiologic and/or surrogate signals may be received from internal or external surrogate sensors, such as surrogate sensors 108 and 120-122. By way of example, sensor 108 may be an accelerometer to measure surrogate information such as activity, or an orientation sensor to measure posture (e.g., whether a person is lying down or standing up). The sensors 120-122 may also be surrogate sensors such as impedance sensors, pressure sensors, pulse oximetry sensors, heart sound sensors, and the like. When measuring surrogate information, the sensors 108, 102-122 produce surrogate signals that represent estimates for at least one of cardiac volume and pressure of the heart. The surrogate signals are collected at the same time as, immediately before or immediately after, the CI measurements are obtained. The surrogate signals may represent at least one of a low frequency component of intracardiac impedance measured along at least one surrogate vector through the heart, an average intracardiac impedance measured along at least one surrogate vector through the heart, heart rate, respiration rate, an activity level of the patient, a posture of the patient, a paced versus sensed rhythm status, and a secondary CI measurement measured along at least one surrogate vector through the heart. As another surrogate, optical pulse arrival time may be used to estimate blood pressure.

Alternatively, the sensors 120-122 may directly measure physiologic parameters, such as a direct measure of blood pressure, or cardiac volume.

The factor module 77 identifies correction factors based on the physiologic and/or surrogate signals as explained below. The correction module 79 applies the correction factors to the contractility estimates to produce contractility trend values over the trending period of time as explained below. The correction module 79 adjusts the contractility estimates, based on the correction factors, to remove non-HF effects. For example, the correction module 79 may remove preload effects from the contractility estimates. Optionally, the correction module 79 may remove after-load effects from the contractility estimates. Optionally, the correction module 79 may remove supply-demand effects from the contractility estimates.

The factor module 77 identifies whether a patient is in a rest state or an active state. The correction module 79 applies a heart rate correction factor when the patient is in the rest state, and applies a cardiac output correction factor when the patient is in the active state. The correction module 79 bins the corrected contractility estimates in CE ranges over a trending period of time to produce trend values. Optionally, the correction module 79 may save the corrected contractility estimates.

Figure 3:
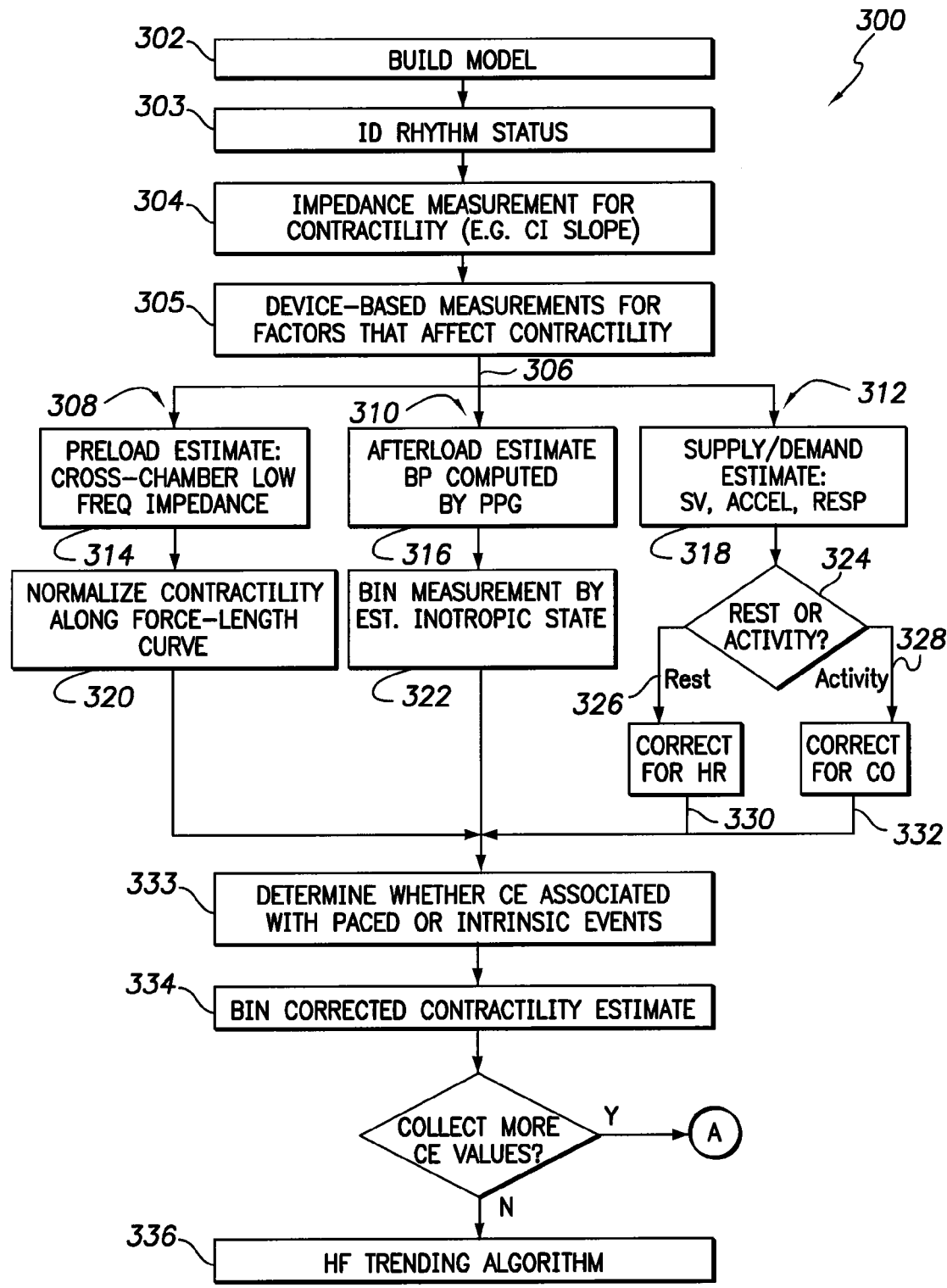
FIG. 3 illustrates a method for trending heart failure based on heart contractility information in accordance with an embodiment.

FIG. 3 illustrates a method 300 for trending heart failure based on heart contractility information in accordance with an embodiment. The method 300 may be performed by the IMD 10, by an external programmer or other computer system. The method 300 begins by building a set or sets of models, at 302, as explained below in more detail in connection with FIG. C. Next, at 303, the method obtains cardiogenic impedance (CI) measurements. The CI measurements may be obtained by an IMD 10 along at least a first vector through the heart (e.g. any one or more vectors shown in FIG. 1). The CI measurements may be obtained at a predetermined measurement interval (e.g. every 30 seconds, every 1 minute, 30 minutes, 1 hour, 5 hours, 1 day, etc.). Alternatively, the CI measurements may be obtained in response to a trigger. For example, when heart rate volume (HRV) crosses a threshold, this may trigger an additional CI measurement. Optionally, when AF is detected or other patient symptoms, these may trigger CI measurement(s). During the measurement interval, the CI measurements may be obtained over a predetermined period of time (e.g. for 10 seconds, 30 seconds, 1 minute, 5 minutes, 30 minutes, 1 hour, 5 hours, etc.). Optionally, the process at 304 may determine CI statistical values for groups of CI measurements (e.g. an average, mean, mode, first standard deviation, second standard deviation, etc.) over the period of time.

The CI measurements may be obtained successively along one of the sensing vectors discussed herein. Alternatively, separate groups of CI measurements may be obtained simultaneously along multiple sensing vectors over the predetermined period of time. When CI measurements are obtained along multiple sensing vectors over the period of time, the CI measurements may be combined for one or more separate vectors to form multiple composite CI waveforms over the period of time. Alternatively, the CI measurements may be combined for all vectors into a single impedance waveform over the period of time. For example, if CI measurements are taken along vectors V1, V2 and V3, the CI measurements may be combined as a weighted sum (e.g., [V1*W1+V2*W2+V3*W3]/3; where W1, W2 and W3 are weighting factors) to form one impedance waveform.

At 304, the method analyzes the waveforms to determine one or more contractility estimates from the CI measurements over the period of time. The contractility estimates relate to the contractility of the heart exhibited over the period of time. Various algorithms may be used to analyze features from CI measurements and derive estimates for contractility therefrom. Various CI features may be used in connection with estimating contractility. Exemplary contractility features, that may be derived from the CI measurements, include peak slope of the waveform, peak-to-valley (max-to-min) amplitude, integral/area-under-curve of the waveform, time from a fiducial point (e.g. R wave) to max or min value and the like. The contractility features can be derived from impedance waveforms taken along one or more CI vectors. By way of example, the peak slope from the impedance waveform, that is obtained from an RV-LV quadpolar vector, may be utilized as a contractility feature for LV dP/dt Max (maximum change in left ventricular pressure per unit time). As another option, the max-to-min values from the impedance waveforms, that are obtained i) along the RV-LV quadpolar vector, ii) along the RA-RV quadpolar vector, and/or iii) along the RA-LV quadpolar vector, may be utilized as representative of, or related to, stroke volume. As another example, the stroke volume may be derived based on the area under the impedance waveform from the CI measurements taken along a bipolar SVC-case vector. Once one or more contractility estimates are obtained, flow moves to 305.

At 305, physiologic and/or surrogate signals are measured by sensor(s) 108 and 120-122. The physiologic and surrogate signals are collectively referred to herein as contractility factors. The contractility factors (physiologic and surrogate signals) correspond directly or indirectly to aspects of the heart state and behavior that effect CI measurements and thus contractility. The surrogate signals represent estimates for at least one of cardiac volume, pressure of the heart, heart rate, a level of patient activity, a posture of the patient and respiration rate. Optionally, the surrogate signals may indicate whether one or more rhythms are paced versus intrinsic rhythms. Alternatively, the sensors 120-122 may directly measure physiologic parameters. The physiologic and/or surrogate signals are measured substantially concurrently with the CI measurements. For example, the physiologic and/or surrogate signals and CI measurements may be obtained simultaneously, over partially overlapping sampling time windows, or over non-overlapping periods of time that are near one another. The physiologic and/or surrogate signals and CI measurements are obtained substantially concurrently in order that the physiologic and/or surrogate signals are representative of the physiologic state or a physiologic parameter of the heart during the period of time, or sampling time window, over which the CI measurements were taken. The signals may be either surrogate signals or direct physiologic signals. However, in either case, they are representative of the physiologic state. The signals, whether direct or surrogate, are themselves surrogates of the physiologic state. For example, blood pressure may be obtained directly from a strain gate pressure transducer in the arterial system, or indirectly (i.e. as a surrogate) from a photoplethysmography signal analysis of pulse arrival time. In either case, a (measured or estimated) systolic blood pressure higher than 140 mmHg would be a surrogate (or indicator) of the increased afterload state.

The contractility factors may be measured by various sensors within or coupled to the IMD 10. For example, the surrogate signals may be produced by the same impedance sensors that obtain the CI measurements, where the surrogate signals are collected immediately before or after the contractility-related CI measurements. Optionally, intracardiac impedance may be collected along surrogate impedance vectors that are separate from, and in addition to, the impedance vectors along which the CI measurements are taken. The dynamic or average impedance is then used as the surrogate signal. The surrogate signals may represent a low frequency component of the impedance measured along at least one surrogate vector through the heart. Alternatively, the surrogate signals may represent average impedance measured along at least one surrogate vector through the heart.

Optionally, the contractility factors may represent a feature or features from the CI measurements other than contractility. In this example, a separate signal need not be measured from the patient. Instead, once the CI measurements are collected, the contractility factors may be obtained by determining, for example, the average value of the CI measurements, the value(s) of the CI measurements at a specific point(s) in time (relative to the cardiac cycle), or by derived features from the CI measurements using different filter settings. For example, the contractility factors may be derived by applying a low-pass filter, a band-pass filter or a high-pass filter to the CI measurements.

Optionally, the contractility factors may include electrical measurements such as IEGM, or detection markers such as pacing pulses or sensed intrinsic events, including both the timing and rates of such measurements/markers. The contractility factors may be obtained from an accelerometer during the minutes preceding a CI measurement, or up to and including the period of time over which the CI measurements are recorded.

Any one or more of the foregoing examples of contractility factors may be used alone or in combination as an input to estimate one or more of a preload effect, an after-load effect, and a supply-demand effect, that the heart may be experiencing during the period of time for which a current CI-based contractility estimate is obtained.

Following the measurements at 304 and 305, flow moves to node 306. At node 306, the process may branch along one or more branches denoted as preload branch 308, after-load branch 310 and supply/demand branch 312. The flow follows one or more of preload branch 308, after-load branch 310 and supply/demand branch 312 serially or in parallel depending upon which type or types of non-HF effects (preload, after-load, and supply-demand) are to be corrected (removed) from the contractility estimates. The branches 308, 310 and 312 seek to identify correction factors, based on the surrogate signals, for preload, after-load, and supply/demand effects, as explained below in more detail. The branches 308, 310 and 312 then apply the corresponding correction factors to the contractility estimates (obtained at 304) in order to remove non-HF effects due to at least one of preload effects, after-load effects and supply-demand effects. The branches 308, 310 and 312 may be applied to each contractility estimate. For example, a contractility estimate may be corrected first for preload, then corrected for after-load and then for supply-demand. The corrected contractility estimates represent contractility trend values that are collected over multiple iterations through the process of FIG. 3.

When flow moves along the preload branch 308, at least a portion of the surrogate signals represents an estimate of end diastolic volume and/or end diastolic pressure. The operations along preload branch 308 remove preload effects from the contractility estimates. Preload effects, relating to at least one of the end diastolic volume and pressure, are caused by stretching of the cardiomyocytes prior to depolarization and contraction. Once preload effects are removed, then flow moves along the after-load branch at 310. At least one of the surrogate signals represents an estimate of blood pressure. The operations along after-load branch 310 remove after-load effects from the contractility estimates. The after-load effects relate to load against which the heart contracts. Once after-load effects are removed, then flow moves along the supply/demand branch at 312, at least one of the surrogate signals may represent estimates of heart rate, stroke volume, and venous and/or arterial blood oxygen saturation. The operations along after-load branch 312 remove supply-demand effects from the contractility estimates. The operations along branch 312 identify whether a patient is in a rest state or an active state. A heart rate correction factor is applied when the patient is in the rest state. A cardiac output correction factor is applied when the patient is in the active state.

Within each of the correction branches 308, 310 and 312, possible factors that confound interpretation of contractility trends are identified at 314, 316 and 318. Then at 320, 322 and 324 the effects of the confounding factors are removed from the contractility estimates in order to leave a "clean" contractility trend of corrected cardiac changes. The clean contractility trend may then be used in diagnosis and prediction of worsening heart failure.

Next, each of the branches 308, 310 and 312 are discussed separately in more detail. The preload branch 308 will be discussed in connection with the graphs at FIGS. 4-8. The "preload effect" varies based on the end diastolic volume or pressure. The end diastolic volume or pressure causes passive stretch in the cardiomyocytes just before depolarization and contraction. As the end diastolic volume or pressure varies (e.g. the amount of preload varies), the amount of stretch in the cardiomyocytes similarly varies, just before depolarization and contraction. When the amount of stretch in the cardiomyocytes varies, the CI measurements similarly vary which in turn causes variation in the contractility estimate. The amount of preload changes (modulates) the amount of contractility exhibited by the heart according to the Frank-Starling mechanism. The Frank-Starling mechanism predicts that increased end diastolic volume yields greater stretch in ventricular fibers at the start of contraction, following a length-force curve. Over a portion of the length-force curve, some amount of stretch leads to increased force production (i.e. higher contractility) whereas overload sets the heart on another (descending) portion of the curve, generating less force (i.e. lower contractility). Preferred A-V timing or increased venous return during exercise, for example, may result in appropriate (normal) increases in preload, whereas heart congestion and impaired forward flow can result in volume overload. When volume overload occurs, this represents pathologically (abnormal) elevated preload.

In a normal healthy heart, the Frank-Starling mechanism predicts that the greater the volume of blood entering the heart during diastole (end-diastolic volume), the greater the volume of blood ejected during systolic contraction (stroke volume) and vice-versa. This allows the cardiac output to be synchronized with the venous return, arterial blood supply and humeral length without depending upon external regulation to make alterations.

Figure 4:
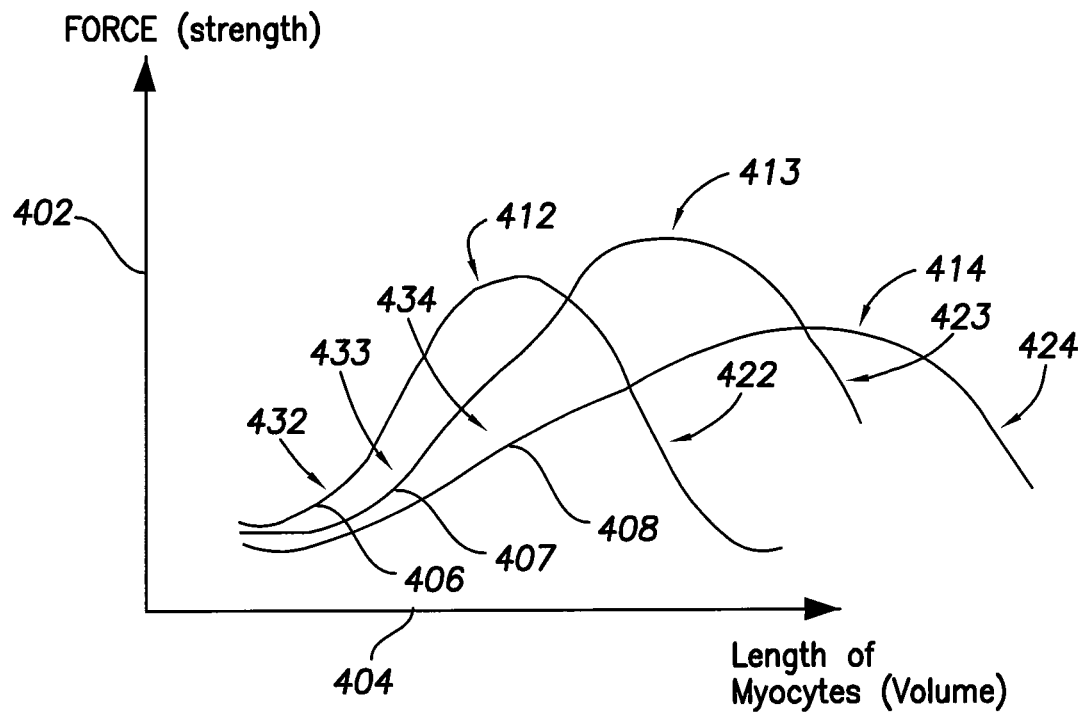
FIG. 4 illustrates exemplary length-force graphs plotting the length of myocytes and the pressure or force that may be collected to build models in accordance with an embodiment.

FIG. 4 illustrates an exemplary graph plotting the active length of myocytes (along the horizontal axis 404) and the generated pressure or force (along the vertical axis 402). The curves in FIG. 4 generally represent the active-tension portion, relating to the amount of stress or force that a myocyte or fiber can generate during contraction. In a more complicated but accurate model, there will also be a "passive length-tension" curve, which is flat and low typically beyond the peak of the active length-tension curve, but then increases sharply at the far right of the length axis. That is to say that as a muscle cell or muscle fiber is greatly over-stretched, it cannot contract as forcefully (descending arm of the active length-tension curve) but remains under high stress due to limitations of the tissue/material itself (passive stress). Thus, for extremely dilated hearts, in addition to failing contraction, there is increased chamber stiffness as well, due to this passive stress phenomenon. As cardiac volume increases, myocytes undergo greater passive stretch, thereby increasing their length. Hence, the length of myocytes correlates to the end diastolic volume of one or more chambers of the heart. In other words, as the end diastolic volume increases, the length of the myocytes similarly increases. Thus, the horizontal axis of FIG. 4 may also represent end diastolic volume.

FIG. 4 illustrates three separate active length-force curves 406-408 which correspond to three different physiologic states of the heart. For example, curve 407 may represent a length-force curve of a heart when in a normal physiologic state. Curve 406 may represent a length-force curve of a heart when in an abnormal pathologic hyper-state. The state associated with curve 406 is referred to as a hyper-state because the amount of force produced is greater than normal for a given myocyte length extension. Curve 408 may represent a length-force curve of a heart when in an abnormal pathologic hypo-state. The state associated with curve 408 is referred to as a hypo-state because the amount of force produced is less than normal for a given myocyte length extension. Each curve 406-408 has a leading portion 432-434 with a rising slope, a peak portion 412-414 and a trailing portion 422-424 with a falling slope.

A heart in a normal physiologic state, exhibits a length-force behavior following curve 407, such that, when the myocytes stretch only a short distance or less than usual at end diastole, for example in hypovolemia or impaired venous return, the myocytes operate along the initial (slightly sloped) segment of the leading portion 433, and produce a relatively low force during contraction. The amount of stretch is relative to the total potential stretch that the myocytes may undergo. The force produced is similarly relative to the maximum total potential force that the myocytes may produce. When the myocytes stretch a medium or normal distance during end diastole, for example when the cardiovascular system is in a euvolemic state, the myocytes operate along the intermediate (steeply sloped) segment of the leading portion 433, and produce a relatively intermediate force during contraction. When the myocytes stretch a long, but still physiologically healthy, distance during end diastole, the myocytes operate along the peak portion 413 (where the slope inverts from positive to negative), and produce a relatively large force during contraction. When the myocytes stretch an excessively long distance during end diastole, for example in a hypervolemic or dilated state, the myocytes are no longer able to produce progressively greater contraction forces. Instead, the myocytes begin to exhibit less contraction force. This behavior is shown along the trailing portion 423 of the curve 407. As the myocytes stretch longer and longer, as shown along the trailing portion 423, the contraction force similarly falls off to a very weak contraction force.

The curves 406 and 408 model the length-force behavior when the heart is in different pathologic states, namely the hyper-state and the hypo-state, respectively. When the heart behaves as if in an above normal force-length state, as shown by curve 406, and the myocytes stretch a short distance during end diastole, the myocytes operate along the initial (slightly sloped) segment of the leading portion 432, and produce a weak force during contraction. When the myocytes stretch a medium distance, the myocytes operate along the intermediate segment of the leading portion 432. When the myocytes stretch a longer distance, the myocytes operate along the peak portion 412, and produce a relatively large force during contraction. When the myocytes stretch an excessively long distance, the contraction force falls off to a very weak force. When curves 406-408 are compared, it is clear that the absolute force created by the myocytes at any given length will vary depending upon which length-force curve appropriately models the state of the heart.

Figure 5:
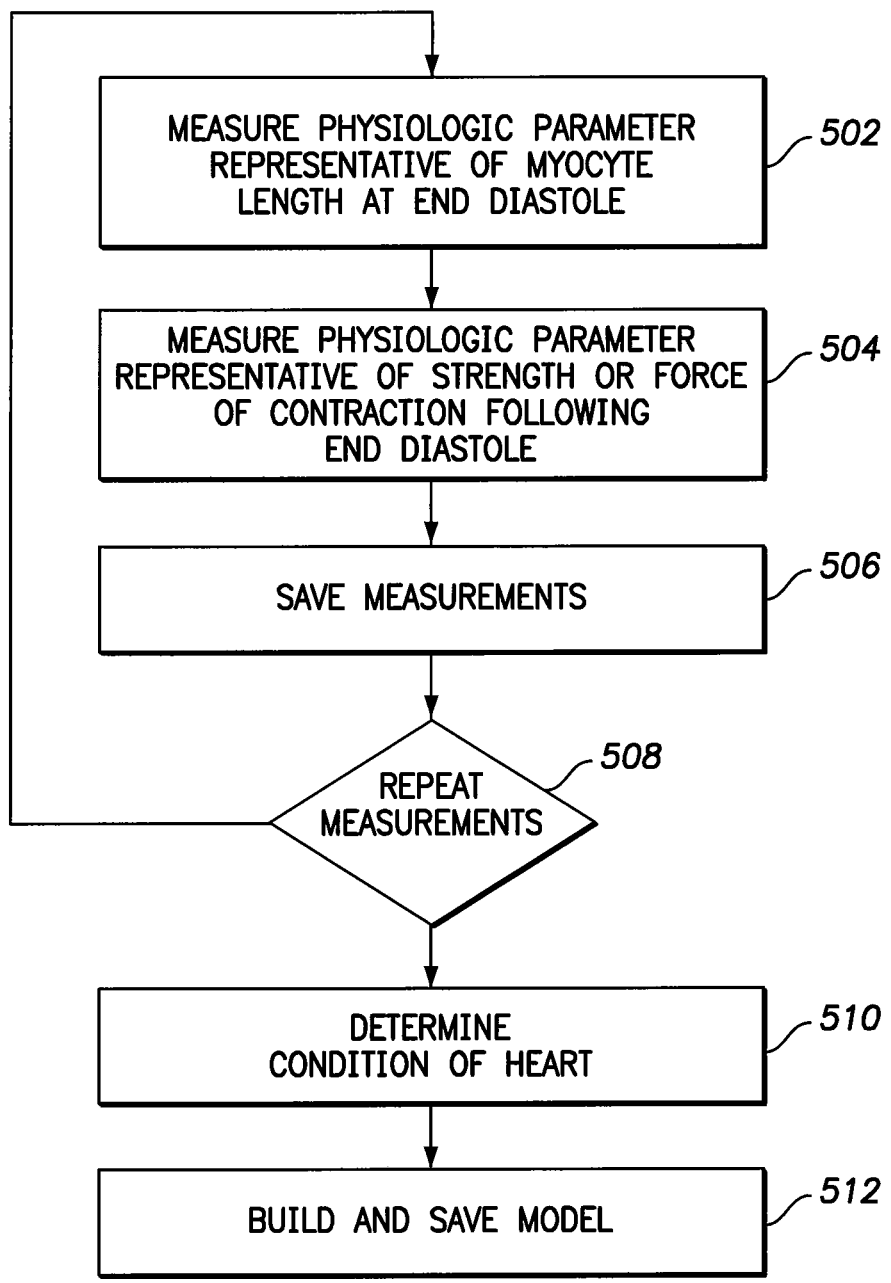
FIG. 5 illustrates a process to build length-force curves that represent models for the behavior of a heart while in various physiologic or pathologic states.

FIG. 5 illustrates a process to build curves that model the behavior of a heart while in various physiologic or pathologic states. For example, length-force curves or another type of curve may be built from data collected from an individual patient over time or during a stress test. Optionally, the curves may be built from data derived from a large population of patients. The process of FIG. 5 may be performed before the process of FIG. 3 in order to build a set or multiple sets of models that are chosen from, and utilized in, 314 and 320 to apply correction factors to the CI measurements.

At 502, the process measures a physiologic parameter or surrogate that is representative of the length for myocytes at the end diastolic stage of the cardiac cycle. For example, the parameter may be cardiac volume which is used to estimate myocyte length. In this example, the cardiac cycle would be monitored to identify end diastole (e.g. through the use of ECG sensors, IEGM sensors, etc.). At end diastole, the process measures cardiac volume, for example by measuring impedance along one or more vectors through the heart and/or aortic vessels. Cardiac volume can be derived from impedance by looking at the RV-LV, RA-RV, or RA-LV impedance vectors. Cardiac volume can be derived from impedance-based large-field flow estimates to get at blood entering pulmonary veins or crossing mitral valve. Cardiac volume can be derived from heart sounds, such as by identifying longer periods of diastosis between the S2 and S1 sounds. Optionally, the amplitude of blood sounds or unusual sounds (e.g., bruit) made by blood may be used to indicate how much LV filling is taking place. In external devices or in clinics, cardiac volume may be derived from ultrasonic or electromagnetic flow probes, ultrasonic sonomicrometry, optical sensors or photometry. When intracardiac impedance is used, the process may use a low pass filter to identify the low frequency content of the intracardiac impedance (Z0) as the estimate of cardiac volume. Alternatively, the process may apply a band-pass filter to identify a frequency band of the cardiogenic impedance (Zc) at the time that corresponds to end diastole. For example, the end diastolic point may be identified based on the R-wave or based on another fiducial marker in the ECG signal.

When the low frequency content of intracardiac impedance Z0 or band-pass cardiogenic impedance, Zc_end-diastole, decrease in value, this indicates greater blood diastolic volume. When low frequency content of intracardiac impedance Z0 or band-pass filtered cardiogenic impedance, Zc_end-diastole, increases, this indicates smaller diastolic blood volume (and greater contribution of myocardium and other surrounding tissues to measured impedance, given the higher conductivity of blood). By way of example, the impedance may be measured along one or more of the RV-LV vector, RA-RV vector, and RA-LV vector. These vectors can be used separately or in combination to estimate impedance along the short and long axis dimensions of the heart. As a further option, quadpolar vectors (e.g., vectors that use different electrodes for drive and sense) may be used instead of bipolar vectors. Quadpolar vectors reduce the effects of interface/tissue contact upon impedance measurements. For example, quad pole vectors may include delivering current between the RV ring and LV ring, while voltage is measured from the RV tip to the LV tip.

As a further option, another vector may be used to obtain impedance measurements, such as supplying a drive current from the RV ring and RA ring to the LV ring (or to several LV rings connected in parallel). In this example, voltage is then measured from the RV tip (and RA tip in parallel) to the LV tip (or to several LV electrodes in parallel). This impedance vector provides an advantageous way to consider both long and short axis contributions to cardiac volume as estimated by impedance.

The correlation between impedance measurements and blood volume is dependent in part on a degree to which the hematocrit and ion concentration in the blood vary. Optionally, the process may include operations to identify the degree of variation in the hematocrit and ion concentration. For example, during the impedance measurement, the process may utilize different frequencies for the impedance drive current (from which impedance measurements are then taken). The frequency for the impedance drive current may be selected to be a frequency that is sensitive to changes in hematocrit or ion concentration. Alternatively or in addition, the process may use other types of sensors, such as optical or chemical sensors, to measure hematocrit and/or ion concentration. When variations in the hematocrit or ion concentration are identified, the impedance measurements may be corrected based on these variations. The foregoing parameters are used to determine myocyte length at end diastole.

At 504, the process measures a physiologic parameter that is representative of the strength or force of contraction during systole, that is, after end diastole. For example, blood pressure may be measured to estimate contraction force. In this example, the cardiac cycle would be monitored to identify end diastole. Immediately after end diastole, or alternately at peak systole, the process would measure blood pressure, for example with a blood pressure sensor. The force or pressure may be determined based on transit time to peak photoplethysmography (PPG) signal.

At 506, the length and force measurements from 502 and 504 are saved, such as in a database. The length and force measurements are correlated with one another, such as by saving timing information for when the measurements were taken and the like.

At 508, the process determines whether it is desirable to repeat 502-506 in order to take additional measurements. It may be desirable to collect a series of length and force measurements over a period of time, referred to as a model building time period, to build a model associated with a given physiologic or pathologic state of the heart. For example, it may be desirable to collect length and force measurements every minute over one or a few hours to build one model. Optionally, the length and force measurements may be obtained less frequently but over a longer data collection period of time to build the model for a corresponding physiologic or pathologic state of the heart. Once a sufficient number of length and force measurements are collected, flow moves to 510.

At 510, the process performs an optional operation, namely it determines the state of the heart while the preceding set of length and heart measurements were collected. For example, it may be determined that the heart is in a normal and at rest physiologic state. It may be determined that the heart is in a normal, but active state. The heart may be determined to be in an abnormal pathologic state. A variety of abnormal states may be identified, in some of which the heart exhibits a length-force behavior associated with a hyper-state and in some of which the heart exhibits a length-force behavior associated with a hypo-state. Optionally, the determination at 510 may be omitted entirely.

At 512, the process builds and saves a model constructed from the length-force measurements collected over the data collection period of time controlled at 508. When a state determination is made at 510, the process labels the model with the corresponding state. Optionally, the models need not be characterized as associated with any particular state.

The operations of 502-512 are repeated during multiple model building time periods to create multiple models for the patient. The process of FIG. 5 may be repeated periodically, or upon direction from a physician or other clinician. Optionally, the process of FIG. 5 may be repeated at points in time when the heart exhibits certain behavioral characteristics indicating that the heart may be in one of a set of predetermined states. Alternatively, the process of FIG. 5 may be repeated in connection with multiple different patients to build a database of general models that are not patient specific. In this latter embodiment, information about the age, disease state, etc., is associated with general aggregate models in the database.

Optionally, the process of FIG. 5 may be implemented with the parameter measured at 502 constituting impedance (e.g., ohms) and the parameter measured at 504 being associated with contractility (e.g., ohms/sec.). In this example, the curve may plot impedance (measured at end diastole) along the horizontal axis and contractility along the vertical axis. As a further option, the horizontal axis may represent decreasing impedance, such that the impedance value decreases as the curve advances along the horizontal axis.

As noted above, the model building process of FIG. 5 is implemented before the contractility collection and correction process of FIG. 3. Returning to FIG. 3, the pre-load correction branch 306 is now discussed in more detail to illustrate how the models (created at FIG. 5) are used to correct contractility for pre-load. The pre-load correction operations 314 and 320 in FIG. 3 are discussed below in more detail in connection with FIG. 6.

Figure 6:
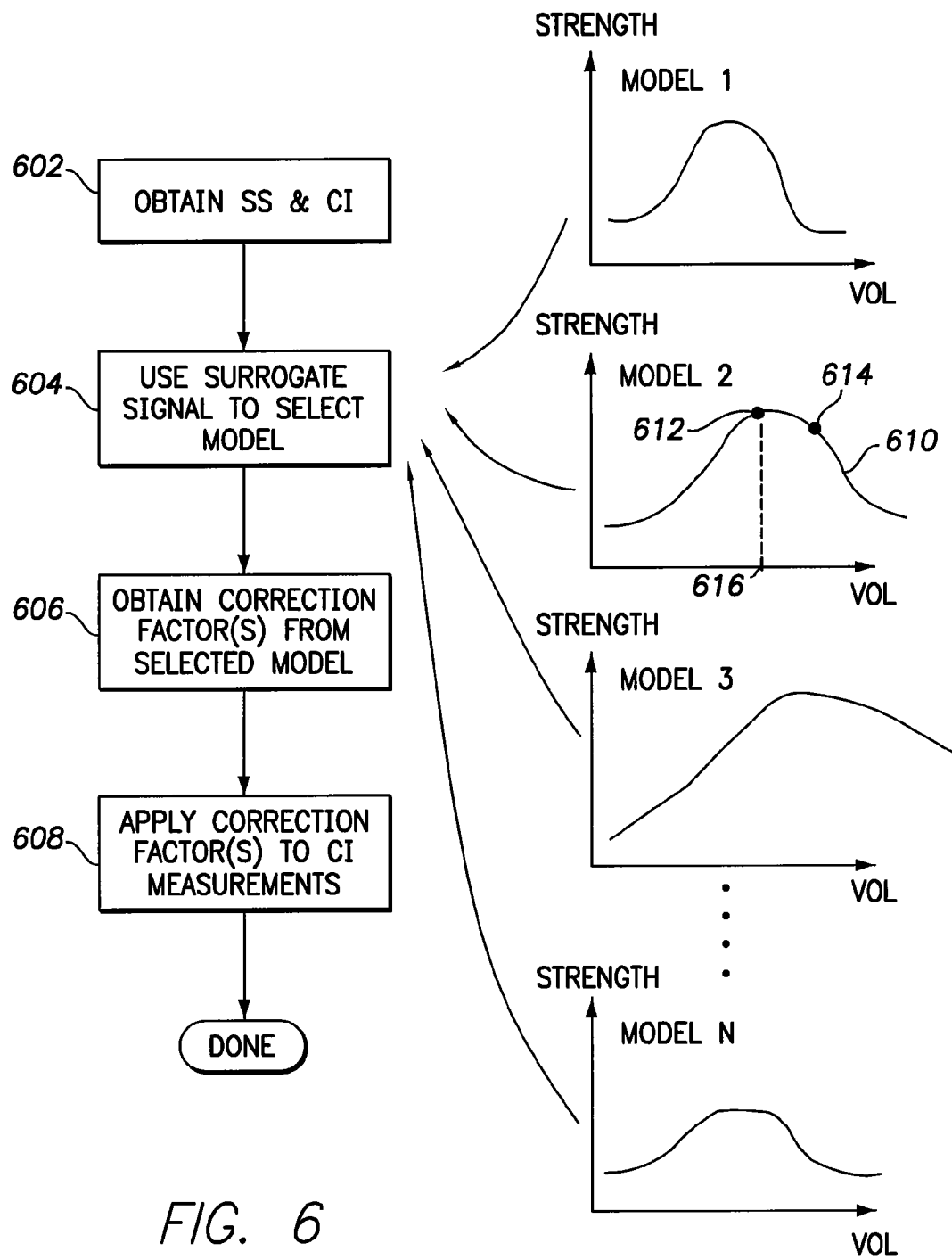
FIG. 6 illustrates a graphical representation of the operations performed to correct for preload in accordance with an embodiment.

FIG. 6 illustrates a graphical representation of the operations performed to correct for preload in accordance with an embodiment. FIG. 6 illustrates a collection of models 1-N that have been generated earlier in time such as in accordance with the process of FIG. 5. At 602, the process accesses the previously acquired surrogate signals and the CI measurements which were obtained at 304 and 305 in FIG. 3.

At 604, the surrogate signals are utilized to identify which of the models 1-N should be used to obtain correction factors. The model may be chosen based on various characteristics of the surrogate signals and the models. For example, the model may be chosen based on a "best fit" or auto-correlation calculation between the models and a series of surrogate signals. It should be recognized that the models 1-N may not directly correlate to the current physiologic or pathologic state of the heart, but instead represent a best or nearest approximation of the current physiologic or pathologic state of the heart. In an embodiment where models collected from many patients are available, the choice of model may be performed based on a constellation of age, gender, body weight or habitus, symptoms, disease etiology or reason for implant, or other factors.

Once a desired model is identified, at 606, the process obtains correction factors from the selected model. In the example of FIG. 6, the models each exhibit a curve that plots contraction strength along the vertical axis and volume at end diastole along the horizontal axis. The volume may be presented in various ways, such as by impedance (ohms) at a select low frequency or within a select frequency band and the like. The contraction strength may be represented in various ways, such as by the change in intracardiac impedance per unit of time (ohms/sec.) at a select low frequency or within a select frequency band and the like.

In the example of FIG. 6, it is assumed that Model 2 has been selected as the preferred match based on the surrogate signals. At 606, the process obtains one or more correction factors from the selected model (e.g. Model 2 denoted at 610). For example, the correction factors may be one or more values along the curve (e.g. 612 and 614). Optionally, the correction factor(s) may represent the slope of the curve 610 at the end diastolic volume (e.g. 616) that corresponds to the current CI measurement to be corrected. As one example, the correction factors 612 and 614 may form a ratio 612/614. As another example, the correction factors 612 and 614 may be combined in another manner (e.g. averaged, subtracted, etc.).

At 608, the correction factors (e.g. 612 and 614) are combined with the CI measurement to correct the CI measurement. For example, the ratio of 612/614 may be multiplied with the CI measurement in order to normalize the CI measurement. Alternatively, a correction factor 612 may be subtracted from the CI measurement. The operation at 608 corresponds to the operation performed at 320 in FIG. 3. At 320, each measure of contractility can be normalized by the "expected" or "maximum" value of contractility given by the curves at the concurrently-noted preload. Once the CI measurement(s) is corrected, flow returns to 334 (FIG. 3).

Returning to FIG. 3, next the after-load correction branch 310 of FIG. 3 will be described in connection with FIG. 7 to correct for after-load effects. The after-load effect typically refers to the load against which the heart contracts. After-load may be represented as the systemic blood pressure. After-load determines how strongly the heart must pump in order to eject blood. In a healthy heart, changes in after-load cause the heart to alter its contractility in order to maintain cardiac output. In the pathologic case, changes in after-load will result in decreases in cardiac output as the sick heart cannot generate the additional pressure required to maintain a desired cardiac output.

In accordance with embodiments herein, various sensors may be used to measure after-load. For example, any sensor may be used that can estimate systemic mean or systolic blood pressure (including but not limited to PPG sensors). Various sensors and techniques may be used for blood pressure estimation, including any available device-based blood pressure estimate.

As explained above in connection with FIG. 3, the after-load contractility factors are obtained/measured concurrently (e.g., on a beat-to-beat basis) with the CI measurements. In embodiments where multiple CI measurements are aggregated (e.g. averaged) or otherwise combined to achieve data reduction, the after-load contractility factors should be similarly averaged or otherwise combined. The value of after-load is stored with the concurrent CI measurement(s) for later trending.

Figure 7:
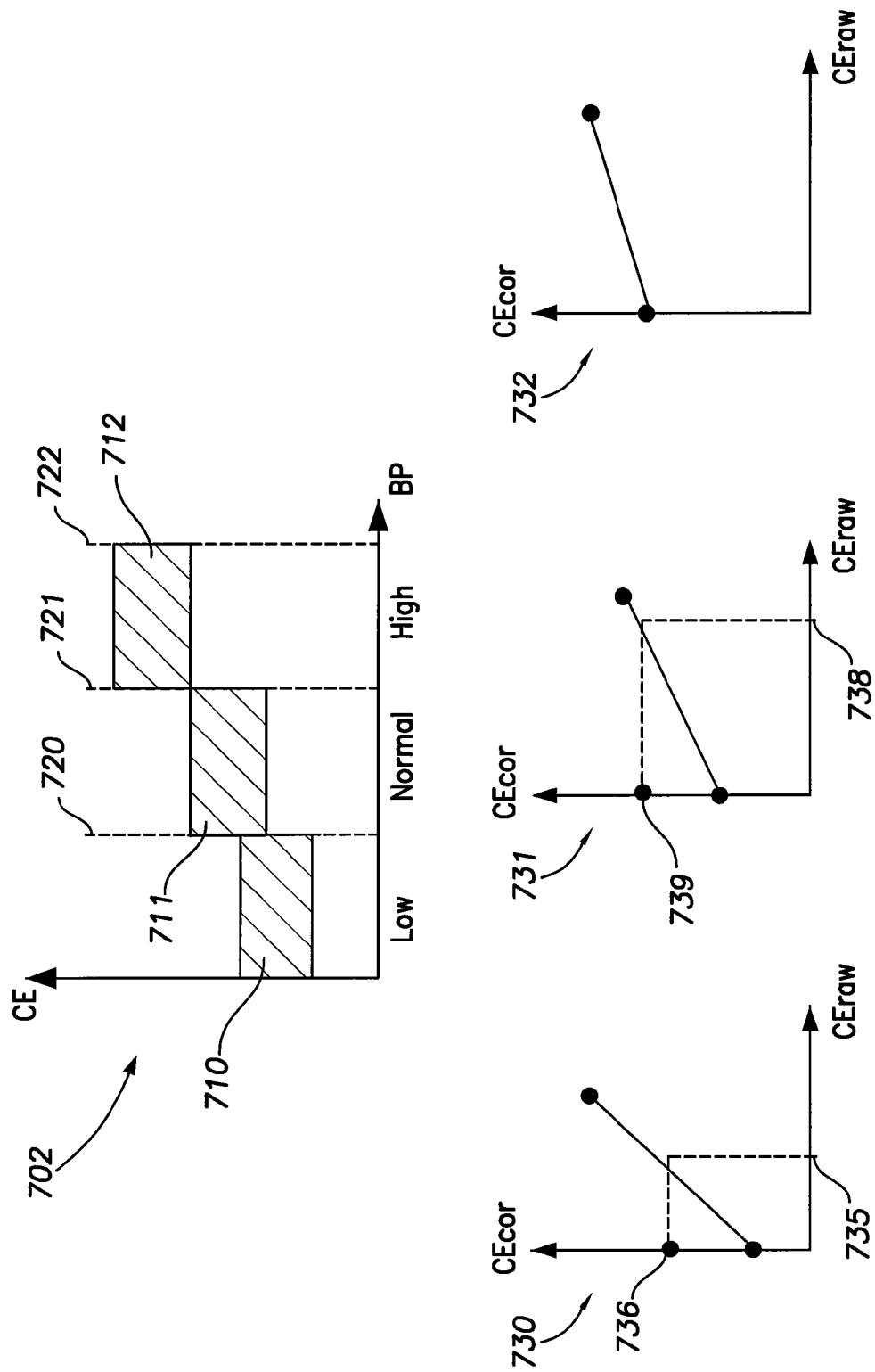
FIG. 7 illustrates a set of graphs that may be used to identify and apply correction factors to the CI measurements.

FIG. 7 illustrates a set of graphs 702, 730-732 that may be used to identify and apply correction factors to the contractility estimates. Graph 702 plots blood pressure along the horizontal axis and contractility estimates along the vertical axis. Graphs 730-732 plot conversion curves that are used to convert a raw contractility estimate (CE) to a corrected CE. The graph 730 is used to correct raw contractility estimates when the blood pressure is low. The graph 731 is used to correct raw contractility estimates when the blood pressure is normal. The graph 732 is used to correct raw contractility estimates when the blood pressure is high.

The graph 702 is separated into 3 regions, namely a first region 710 corresponding to a low blood pressure state, a second region 711 corresponding to a normal blood pressure state, and a third region 712 corresponding to a high blood pressure state. During the process of FIG. 3, the surrogate signals (obtained at 304) are used at 316 to identify the patient's blood pressure. At 316, the measured blood pressure is classified as low, normal or high based on the blood pressure cut-offs 720-722 (FIG. 7) between the regions 710-712. The regions 710-712 are associated with different conversion relations which are illustrated in curves 730-732, respectively. When the blood pressure is low, the process selects at 316 the conversion relation associated with curve 730. When the blood pressure is normal, the process selects at 316 the conversion relation associated with curve 731. When the blood pressure is high, the process selects at 316 the conversion relation associated with curve 732.

In the example of FIG. 7, the curves 730-732 are linear, have different y-intercepts and have different slopes. Optionally, the curves 730-732 may be non-linear. The curves 730-732 may be set by a physician or clinician. The curves 730-732 may be set based on contractility estimates taken from the individual patient, or based on a collection of prior patients.

Once one of the curves 730-732 is chosen, the process of FIG. 3 then applies at 322 the raw contractility estimates to the appropriate curve to determine corrected contractility estimates. By applying the conversion from one of curves 730-732, the process at 322 corrects the contractility estimate based on the inotropic state of the heart. By way of example, if the patient's blood pressure is low, then region 710 is selected, which corresponds to conversion curve 730. The raw contractility estimates may be 735, which corresponds to a corrected contractility estimates 736. Alternatively, if the patient's blood pressure is normal, then region 711 is selected, which corresponds to conversion curve 731. The raw contractility estimates may be 738, which corresponds to a corrected contractility estimates 739

As noted above, the graphs 702 and 730-732 are built before the process of FIG. 3. The graphs 702 and 730-732 are used at 316 and 322 in order to correct contractility estimates based on the inotropic state of the heart (e.g., low, normal or high blood pressure) when collecting the CI measurements, from which the contractility estimates were derived.

Once the contractility estimate is corrected, flow moves to 334, where the corrected contractility estimate is binned into the appropriate trend value bin or trend range bin.

Changes in contractility resultant from afterload should be normalized so as to generate an afterload-independent contractility estimate. For example, end systolic pressure volume relation gives an indication of maximum contractility at a given inotropic state. If the afterload measure changes slightly on a beat-to-beat basis and the contractility is assumed constant over such a short period of time, then the inotropic state can be removed from the contractility estimate by dividing the contractility estimate by each beat's afterload measure. At the time of trend analysis, the afterload-corrected slope rather than the "raw" contractility estimate should be the parameter to be trended/compared. As the afterload-corrected slope decreases, it indicates worsening heart failure and/or further progression of disease.

Next, the supply-demand correction branch 312 of FIG. 3 will be described to correct for supply and demand effects. During normal function, as muscles use up and require more oxygen, both heart rate and stroke volume can increase. These increases are also accompanied by increased contractility. During pathologic function, heart rate, but not stroke volume, may increase to provide the required oxygen to the body.

At 304, one of the surrogate signals may be a measure of impedance-based stroke volume to estimate supply versus demand. Optionally, other estimates of stroke volume may be used to estimate supply versus demand, such as pulse amplitude or integral of a PPG signal, stored at or near the time of a CI measurement. Concurrently with CI measurements, surrogate signals are measured from sensors that detect the heart rate and patient activity. The heart rate and activity sensors are used to estimate supply versus demand. For example, the stroke volume surrogate signal may be multiplied with the heart rate to yield an instantaneous cardiac output surrogate that is then associated with each contractility estimate. Another method would incorporate a mixed venous oxygen saturation sensor, for example an optical sensor on an RV lead or in the pulmonary artery. As the venous saturation drops relative to the arterial saturation (arterial can be measured, estimated, or assumed—but assumptions would only hold for short time periods), the suggestion is that cardiac output is lower than it could or should be. On the other hand, if venous oxygen saturation remains high despite increased activity, the heart is effectively providing enough blood supply (cardiac output) to the muscles.

When heart rate increases without a change in stroke volume, then any changes in contractility may be attributed substantially entirely to the force-frequency or Treppe effect. In this example, the change in heart rate is considered secondary to supply. Changes in heart rate concurrent with changes in stroke volume typically result in larger overall changes in cardiac output. Changes in contractility in this case are attributable both to Treppe effect and to catecholamine or other wide-ranging responses associated with normal physiology. The rate change is considered secondary to demand.

Optionally, the estimate for demand may be based on surrogate signals related to respiration, such as from a minute ventilation sensor, based on changes in IEGM signals, based on a Zr impedance signal and the like. For example, when the respiration rate increases and breathing is deeper, typically there will be an increase in demand. However, when the breathing rate remains rapid and shallow or does not change, typically this indicates that increases in heart rate are due to abnormal pathologic factors.

The activity of a patient may be determined by an activity sensor (e.g., an accelerometer) which indicates when patient activity causes an increased oxygen demand. The output of the activity sensor can serve as an independent surrogate signal for estimating demand. That is, if the activity sensor indicates exercise, then the other supply/demand sensors become less important since an increase in cardiac output is expected (demand indicated). When the activity sensor indicates rest and yet the heart rate still increases, particularly during labored breathing and without changes in stroke volume, then associated changes in contractility are significant indicators of potential heart failure.

Returning to FIG. 3, when flow moves along branch 312, the contractility factors at 318 represent a signal indicative of stroke volume, an activity signal and a respiration rate signal.

At 324, the activity signal is analyzed to determine whether the patient is in an active state or in a rest state. When in an active state, flow moves along path 328 to 332. When in an at rest state, flow moves along path 326 to 330. At 332, the contractility estimate is corrected (e.g., normalized) based on heart rate. If a force-frequency relation curve is generated by rate modulation alone, for example by atrial-only pacing at slightly elevated rates while the patient is asleep or at rest, then estimates of the Treppe effect on contractility can be modeled (just as in the cases of modeling effects of preload or afterload). In such model, heart rate is on the horizontal axis and contractility is on the vertical axis. Then, once a model is present to account for Treppe effect, new signals are placed on the same set of axes based on heart rate. If the contractility falls on the model curve, the change in contractility is deemed to have occurred secondary to rate alone, and the corrected signal will follow the same curve to whatever "nominal rate" is used for the correction. If, however, the new contractility data point is above the curve, then there are both rate and CO effects. The rate effects can be factored out by following parallel to the Treppe curve back to the nominal heart rate. The stroke volume portion would be corrected ratiometrically, for example dividing out a "baseline" stroke volume after the rate correction.

The effects of supply/demand on contractility are corrected within the contractility estimates somewhat differently at 330 and 332. An increase in demand due to exercise or normal physiologic changes can be expected to increase contractility. On the other hand, "apparent" increases of demand may actually be decreases of supply in the pathologic case of poor cardiac performance. Thus, when the activity sensor indicates exercise and/or when the heart rate and stroke volume surrogate move together, the contractility estimate is normalized to the cardiac output. When the activity sensor indicates rest and/or when the heart rate increases without changes in stroke volume, the contractility estimate is normalized to heart rate alone. After this dichotomous normalization, the corrected contractility trend value can be evaluated on a level playing field, such that true demand-independent changes in contractility can be identified. Optionally, given that cardiac output equals stroke volume times heart rate (CO=SV*HR), the method may normalize contractility based on cardiac output. During heart fail progression, stroke volume will also change accordingly, and the heart capability during exercise is decreased so that CO during activity versus CO during rest has a smaller difference. Optionally, the difference in CO between an at rest state and an exercise state may be used as an indicator to correct contractility estimates.

Optionally, the process at branch 312 may be done in parallel with the above example that uses changes in CO between at rest and exercise states.

Referring to FIG. 3, at 333, the process determines whether the contractility estimate (CE) corrected along branches 308, 310 and 312, was derived from CI measurements taken during a cardiac cycle that includes one or more paced events (rhythm) or during a cardiac cycle that includes only intrinsic events. When a corrected CE is derived from a paced rhythm, the CE is labeled as a paced CE and is subsequently binned (at 334) with CEs from paced rhythms. When the corrected CE is derived from an intrinsic rhythm (having no paced events in the cardiac cycle), the CE is labeled an intrinsic CE and is subsequently binned (at 334) with CEs from other intrinsic rhythms.

At 334, the corrected contractility estimates are saved. For example, contractility trend values may be saved in bins where each bin is defined by a contractility trend value or a range of contractility trend values. Each time a contractility trend value is identified that falls within a particular bin, a count associated with that bin is incremented at 334. By utilizing bins to count corrected contractility estimates, the method avoids saving each individual trend value, thereby saving memory space. Optionally, when memory is available, the operation at 334 may save the individual contractility trend values over a trending time range. The operations between 304 and 334 are repeated over a predetermined trend period of time. For example, 304 to 334 may be repeated at predetermined periods of time over 24 hours, over a week, over a month, etc. or other trending time range. Once the operations at 304 to 334 collect a sufficient amount of corrected contractility estimates, flow moves to 336.

At 336, an HF trending process is performed based on the saved or binned corrected contractility estimates. The HF trending process may include analyzing and/or displaying a series of contractility trend values or bins for trend values as a heart failure trend over the trending period of time.

In one embodiment, the CI measurements taken during paced rhythm are binned and compared only with CI measurements taken during other paced rhythms. Similarly, CI measurements taken during intrinsic rhythm are binned and compared in like manner with CI measurements taken during other intrinsic rhythms. Further, if upon inspection of trend data there is still too much variance to draw conclusions, data may be binned and compared only with other data recorded at similar posture (determined by the 3D accelerometer) and/or at similar time-of-day (by the date stamp associated with each recording). Any "bin" comprising less than a threshold amount of data (e.g., about 5%) of the total number of samples may be excluded.

Figure 8:
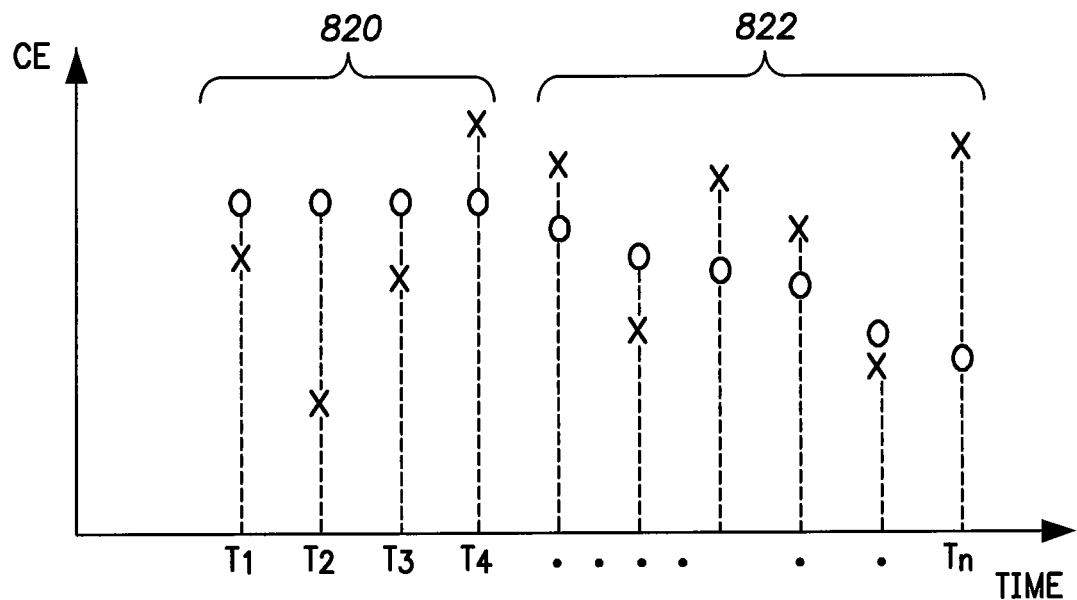
FIG. 8 illustrates an exemplary plot of raw and corrected contractility estimates over time.

FIG. 8 illustrates an exemplary plot of contractility estimates (along the vertical axis) over time (along the horizontal axis). In FIG. 8, the "X"s denote "raw" un-corrected contractility estimates taken at times T1-Tn. As evident from FIG. 8, the raw un-corrected contractility estimates X vary widely and do not exhibit a clear indication of any particular trend. The time line may represent a few minutes, several hours, several days, months and the like.

In FIG. 8, the "O"s denote corrected contractility estimates associated with each of the raw contractility estimates X at times T1-Tn. The preload correction process of FIG. 6 is repeated at each of times T1-Tn, to select a model (model 1-model N), identify and apply a correction factor(s). By way of example, model 1 may be selected and used at times T1 and T4, while a model 2 may be selected and used at times T2 and T3. Additional models may be selected and used at other times up to time Tn. The corrected contractility estimates O follow a clear trend with an initial portion 820 that is relatively flat followed by a declining tail portion 822. As shown in FIG. 8, by using models 1-N and applying correction factors, the corrected contractility estimates show a clear trend, namely decreasing CI. Decreased cardiogenic impedance is a good indicator of decreased blood volume at end diastole. The decline in blood volume at end diastole represents a good indicator that the patient may be experiencing heart failure.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for trending heart failure (HF) based on heart contractility information, comprising:
measuring cardiogenic impedance (CI) measurements along at least a first vector through a heart over a period of time;
determining contractility estimates from the CI measurements, the contractility estimates relating to contractility of the heart;
obtaining contractility factors representing estimates for or direct measurements of at least one of cardiac volume and pressure of the heart when the CI measurements were obtained;
identifying correction factors based on the contractility factors;
applying the correction factors to the contractility estimates to produce contractility trend values over the period of time; and
applying therapy to the heart to optimize contractility of the heart as a function of the trend values.

2. The method of claim 1, further comprising illustrating a series of contractility trend values as a heart failure trend over the period of time.

3. The method of claim 1, wherein the applying operation adjusts the contractility estimates, based on the correction factors, to remove non-HF effects due to at least one of preload effects, after-load effects and supply-demand effects.

4. The method of claim 1, wherein the contractility factors are surrogate signals that represent estimates of end diastolic volume, wherein the CI measurements and associated surrogate signals are obtained concurrently and the applying operation removes preload effects from the contractility estimates, the preload effects relating to at least one of the end diastolic volume and pressure which results in stretching of cardiomyocytes prior to depolarization and contraction.

5. The method of claim 1, wherein the contractility factors are surrogate signals that represent estimates of blood pressure, wherein the CI measurements and associated surrogate signals are obtained concurrently, and the applying operation removes after-load effects from the contractility estimates, the after-load effects relating to load against which the heart contracts.

6. The method of claim 1, wherein the contractility factors are surrogate signals that represent estimates of heart rate and stroke volume, wherein the CI measurements and associated surrogate signals are obtained concurrently and the applying operation removes supply-demand effects from the contractility estimates.

7. The method of claim 1, wherein the contractility factors are surrogate signals that represent estimates of at least one of heart rate, stroke volume, blood oxygen saturation, patient activity and respiration and wherein the CI measurements and associated surrogate signals are obtained concurrently to ascertain differences between changes in demand versus supply of oxygen.

8. The method of claim 1, wherein the identifying operation further comprises determining whether a patient is in a rest state or an active state, the applying operation applies a heart rate correction factor when the patient is in the rest state, the applying operation applies a cardiac output correction factor when the patient is in the active state.

9. The method of claim 1, wherein the contractility factors are surrogate signals that represent at least one of a low frequency component of intracardiac impedance measured along at least one surrogate vector through the heart, an average intracardiac impedance measured along at least one surrogate vector through the heart, heart rate, respiration rate, an activity level of the patient, a posture of the patient, a paced versus sensed rhythm status, and a secondary CI measurement measured along at least one surrogate vector through the heart.

10. The method of claim 1, wherein the contractility factors are surrogate signals that are obtained by identifying features from the CI measurements.

11. A system for trending heart failure (HF) based on heart contractility information, comprising:
inputs to receive cardiogenic impedance (CI) measurements taken along at least a first vector through a heart over a period of time;
a contractility module to determine contractility estimates from the CI measurements, the contractility estimates relating to contractility of the heart;
a collection module to receive contractility factors representing estimates for or direct measurements of at least one of cardiac volume and pressure of the heart when the CI measurements were obtained;
a factor module to identify correction factors based on the contractility factors; and
a correction module to apply the correction factors to the contractility estimates to produce contractility trend values over the period of time.

12. The system of claim 11, wherein the correction module adjusts the contractility estimates, based on the correction factors, to remove non-HF effects due to at least one of preload effects, after-load effects and supply-demand effects.

13. The system of claim 11, wherein the contractility factors are surrogate signals that represent estimates of end diastolic volume, wherein the CI measurements and associated surrogate signals are obtained concurrently and the correction module removes preload effects from the contractility estimates, the preload effects relating to at least one of the end diastolic volume and pressure which results in stretching of cardiomyocytes prior to depolarization and contraction.

14. The system of claim 11, wherein the contractility factors are surrogate signals that represent estimates of blood pressure, wherein the CI measurements and associated surrogate signals are obtained concurrently, and the correction module removes after-load effects from the contractility estimates, the after-load effects relating to load against which the heart contracts.

15. The system of claim 11, wherein the contractility factors are surrogate signals that represent estimates of heart rate and stroke volume, wherein the CI measurements and associated surrogate signals are obtained concurrently and the correction module removes supply-demand effects from the contractility estimates.

16. The system of claim 11, wherein the contractility factors are surrogate signals that represent estimates of at least one of heart rate, stroke volume, blood oxygen saturation, patient activity and respiration and wherein the CI measurements and associated surrogate signals are obtained concurrently to ascertain differences between changes in demand versus supply of oxygen.

17. The system of claim 11, wherein the factor module identifies whether a patient is in a rest state or an active state, the correction module applying a heart rate correction factor when the patient is in the rest state, the correction module applying a cardiac output correction factor when the patient is in the active state.

18. The system of claim 11, wherein the contractility factors are surrogate signals that represent at least one of a low frequency component of intracardiac impedance measured along at least one surrogate vector through the heart, an average intracardiac impedance measured along at least one surrogate vector through the heart, heart rate, respiration rate, an activity level of the patient, a posture of the patient, a paced versus sensed rhythm status, and a secondary CI measurement measured along at least one surrogate vector through the heart.

19. A system for trending heart failure (HF) based on heart contractility information, comprising:
means for measuring cardiogenic impedance (CI) values along at least a first vector through a heart over a period of time;
means for determining contractility estimates from the CI values, the contractility estimates relating to contractility of the heart;
means for obtaining contractility factors representing estimates for or direct measurements of at least one of cardiac volume and pressure of the heart when the CI values were obtained;
means for identifying correction factors based on the contractility factors; and
means for applying the correction factors to the contractility estimates to produce contractility trend values over the period of time.

* * * * *